United States Patent
Zhong

(10) Patent No.: US 6,179,817 B1
(45) Date of Patent: Jan. 30, 2001

(54) HYBRID COATING FOR MEDICAL DEVICES

(75) Inventor: Sheng-Ping Zhong, Northboro, MA (US)

(73) Assignee: Boston Scientific Corporation, Natick, MA (US)

( * ) Notice: Under 35 U.S.C. 154(b), the term of this patent shall be extended for 0 days.

(21) Appl. No.: 09/238,707

(22) Filed: Jan. 28, 1999

Related U.S. Application Data

(63) Continuation-in-part of application No. 08/877,825, filed on Jun. 18, 1997, now Pat. No. 5,869,127, which is a continuation-in-part of application No. 08/392,141, filed on Feb. 22, 1995, now Pat. No. 5,702,754.

(51) Int. Cl.$^7$ .................... A61J 3/00; C08F 283/00; A01N 1/00
(52) U.S. Cl. ................ 604/265; 427/2.3; 427/2.24; 525/54.2; 523/112
(58) Field of Search ................ 427/2.1, 2.13, 427/2.24, 2.3; 604/265; 525/54.2; 523/112

(56) References Cited

U.S. PATENT DOCUMENTS

| | | |
|---|---|---|
| 4,069,352 | 1/1978 | Parsons, Jr. . |
| 4,119,094 | 10/1978 | Micklus et al. . |
| 4,500,676 | 2/1985 | Balazs et al. . |
| 5,037,677 | 8/1991 | Halpern et al. . |
| 5,041,100 | 8/1991 | Rowland et al. . |
| 5,049,393 | 9/1991 | Noon et al. . |
| 5,061,750 | 10/1991 | Feijen et al. . |
| 5,133,742 | 7/1992 | Pinchuk . |
| 5,163,958 | 11/1992 | Pinchuk . |
| 5,263,992 | 11/1993 | Guire . |
| 5,272,012 | 12/1993 | Opolski . |
| 5,282,823 | 2/1994 | Schwartz et al. . |
| 5,342,348 | 8/1994 | Kaplan . |
| 5,342,621 | 8/1994 | Eury . |
| 5,350,800 | 9/1994 | Verhoeven et al. . |
| 5,360,397 | 11/1994 | Pinchuk . |
| 5,383,928 | 1/1995 | Scott et al. . |
| 5,449,382 | 9/1995 | Dayton . |
| 5,464,450 | 11/1995 | Buscemi et al. . |
| 5,496,581 | 3/1996 | Yianni et al. . |
| 5,541,167 | 7/1996 | Hsu et al. . |
| 5,571,166 | 11/1996 | Dinh et al. . |
| 5,575,818 | 11/1996 | Pinchuk . |
| 5,591,224 | 1/1997 | Schwartz et al. . |
| 5,599,352 | 2/1997 | Dinh et al. . |
| 5,800,541 | * 9/1998 | Rhee et al. ............... 623/11 |
| 5,874,417 | * 2/1999 | Prestwich et al. ........ 514/54 |
| 5,897,955 | * 4/1999 | Drumheller ............. 428/422 |
| 5,955,588 | * 9/1999 | Tsang et al. ............ 427/2.25 |
| 5,972,199 | * 10/1999 | Heller et al. ........... 205/777.5 |

FOREIGN PATENT DOCUMENTS

| | | |
|---|---|---|
| 389 632 A1 | 10/1990 | (EP) . |
| 496 305 A2 | 7/1992 | (EP) . |
| 627 226 A1 | 12/1994 | (EP) . |
| WO 91/19756 | 12/1991 | (WO) . |
| WO 92/19289 | 11/1992 | (WO) . |
| WO 92/19290 | 11/1992 | (WO) . |
| WO 97/33552 | 9/1997 | (WO) . |

* cited by examiner

*Primary Examiner*—Shrive Beck
*Assistant Examiner*—Jennifer Kolb
(74) *Attorney, Agent, or Firm*—Hoffmann & Baron, LLP

(57) ABSTRACT

Disclosed are hybrid coatings for implantable medical devices. Such coatings include a first layer of an aqueous dispersion or emulsion of an organic acid functional group containing polymer, a crosslinker and a therapeutic agent dispersed therein. The coating also includes a second layer of an aqueous solution or dispersion of an organic acid functional group-containing bio-active agent. The hybrid coatings are especially suited for preventing restenosis of endoprostheses by the combined action of the therapeutic agent and the bio-active agent. Methods of making and using devices coated with such compositions are also provided.

34 Claims, No Drawings

HYBRID COATING FOR MEDICAL DEVICES

CROSS-REFERENCE TO RELATED APPLICATIONS

This application is a continuation-in-part of U.S. Ser. No. 08/877,825 filed Jun. 18, 1997 now U.S. Pat. No. 5,869,127 which is a continuation-in-part of U.S. Serial No. 08/392,141, filed Feb. 22, 1995 now U.S. Pat. No. 5,702,754 both of which are incorporated by reference herein.

FIELD OF INVENTION

This invention relates generally to bio-compatible substrate coatings. More particularly, the present invention relates to bio-compatible coating compositions for delivering therapeutic agents in vivo. Methods of enhancing the bio-compatibility of a substrate and of delivering a therapeutic agent in vivo through these coatings, as well as devices incorporating such coatings are also described.

BACKGROUND OF THE INVENTION

It is generally known to provide a substrate, such as a medical device or parts of such a device with bio-active coatings for the purpose of enhancing the bio-compatibility of the device when it is introduced into a mammal, such as a human body. Furthermore, it is generally known that various additives, such as therapeutic agents, can be introduced into as substrate for the purpose of releasing such additives into a mammal, such as a human body.

Endoprostheses used for minimally invasive procedures in body conduits, such as, for example, in blood vessels may be provided with bio-active coatings and may also be provided with a means to releasably incorporate a therapeutic agent. Vascular grafts, stents and graft-stent combinations are specific examples of such endoprostheses. Other useful devices include catheters, guide wires, trocars, introducer sheaths and the like.

A therapeutic agent can be incorporated into a substrate and the substrate can be implanted to provide localized delivery of the therapeutic agent. For example, U.S. Pat. No. 5,651,986 discloses a method for administering a therapeutic agent to inhibit growth of a solid tumor. The delivery of the therapeutic agent is accomplished by implanting a device proximally to the tumor where the agent is encapsulated in a biocompatible matrix on the surface of or throughout the implant. The agent is typically released by diffusion, degradation of the matrix, or a combination thereof.

Delivery of other therapeutic agents, such as taxol, is also possible. For example, U.S. Pat. No. 5,733,925 discloses a delivery system for administering taxol by encapsulating the taxol in a polymer. To encapsulate the taxol, the polymer is dissolved in a halogenated hydrocarbon solvent. The encapsulated taxol is implanted where it can be dispersed by the above-mentioned techniques.

Delivery systems for therapeutic agents can be incorporated into other, medical devices, such as a stent. International Patent Application No. PCT/US96/02125 discloses biodegradable compositions that can coat a stent and can be impregnated with a therapeutic agent. The compositions are polymers derived from the condensation of alpha hydroxycarboxylic acids and related lactones, e.g., polylactides or polyglycolides. To form the coating with a therapeutic agent, the polymer must be dissolved in a halogenated hydrocarbon solvent and the therapeutic agent is then dispersed into the solvent/polymer mixture.

The use of solvents is not limited devices that are by themselves or are incorporated as, delivery system for therapeutic agents. Medical articles or devices coated with hydrophilic coatings have been described in a number of references, some of which are discussed below. These patents all employ the use of solvents and/or the requirement for high temperature curing.

U.S. Pat. No. 4,119,094 discloses a method of coating a substrate with a polyvinylpyrrolidone-polyurethane interpolymer. In this method, a polyisocyanate and a polyurethane in a first solvent, such as, methyl ethyl ketone are applied to a substrate. The first solvent is then evaporated and polyvinylpyrrolidone in a second solvent is applied to the treated substrate. The second solvent is then evaporated.

International Patent Applications Nos. PCT/EP92/00918, PCT/EP92/00919 and PCT/DK92/00132 disclose methods for providing medical devices having polyurethane surfaces with a hydrophilic coating of poly(meth)acrylamide. Before application of the hydrophilic coating to the poly(meth)acrylamide substrate surface, it is treated with a compound having functional groups capable of reacting with the polyurethane and the poly(meth)acrylamide, respectively. This compound is typically a di- or higher isocyanate functionality in an organic solvent.

U.S. Pat. No. 5,272,012 discloses a method for applying a protective, lubricious coating to a surface of a substrate. The coating described by the '012 patent includes aprotective compound, such as a urethane; a slip additive, such as a siloxane; and an optional crosslinking agent, such as a polyfunctional aziridine. The surface of a substrate coated with such a composition, however, is not continuously lubricious. Such a coating contains separate physical domains of lubriciousness interspersed within a protective matrix, rather than a continuous layer of a lubricious agent.

U.S. Pat. No. 5,037,677 discloses a method of interlaminar grafting of continuous, hydrophilic anti-fogging coatings for acrylic intra-ocular lenses. Such a method is accomplished using at least two laminae which are not mutually soluble. For example, the '677 patent describes preparing a solution of a copolymer of ethyl methacrylate, butyl acrylate and hydroxyethyl methacrylate in an ethoxy ethyl acetate organic solvent. To this solution is added a molar excess of polyisocyanate. This solution is applied to a plexiglass substrate which is placed in a vacuum oven, where a prepolymer is formed from the two solutes while the ethoxyethyl acetate solvent is evaporated. A 0.2% sodium hyaluronate solution is then applied to the surface of the plexiglass.

The plexiglass is then returned to an oven wherein the hydroxyl groups of the Na-hyaluronate react with the isocyanate groups in the prepolymer layer. Coatings formed in such a manner as the '677 patent suffer from the drawback that organic solvents and/or other toxic chemicals are used as carriers which, if not completely removed prior to introduction of the substrate into the body, can deleteriously react in vivo to cause inflammation, blood clotting and other undesirable side effects. Thus, in order to avoid the use of such organic solvents, some non-solvent methods have been developed.

For example, EP Pat. Application Nos. 92100787.8 and EP 0496 305 A2 disclose methods for preparing a shaped medical. article with a lubricous coating. In these methods, a coating composition that includes a blend of polyurethane and polyvinylpyrrolidone is co-extruded with a substrate polymer to produce a shaped article having on a surface thereof a layer of the coating composition which becomes lubricous when contacted with water.

U.S. Pat. No. 5,041,100 discloses a method for coating a substrate with a mixture of poly(ethylene oxide) and an aqueous dispersion of a structural plastic material, e.g. polyurethane. As an example, this patent discloses a non-crosslinked admixture of poly(ethylene oxide) and a structural plastic material. This composition provides a hydrophilic character to the substrate which may leach to the surface thereof, or be entrapped adjacent to the surface to provide a hydrophilic, reduced friction character thereto, particularly when hydrated.

The methods in the above-described references suffer from the drawback that inter-polymer networks which physically attach hydrophilic polymers to their substrates often break down upon prolonged turbulent flow or soaking. Furthermore, the hydrophilic species are weakly attached to their substrates and can be easily washed away, thereby rendering the underlying article insufficiently lubricous.

International Pat. Application No. PCT/DK91/00163, co-owned with the present invention, discloses a method of providing a medical instrument with a hydrophilic, low-friction coating. This method includes the steps of (1) forming an inner layer on the substrate from an aqueous polymer emulsion, (2) forming an outer layer on top of the inner layer from an aqueous solution of a water-soluble hydrophilic polymer and (3) curing the two layers simultaneously by heating to a temperature above 100° C.

Although the use of organic solvents is eliminated in this method, high curing temperatures must be applied to bond the inner layer to the outer layer. These high curing temperatures are not useful on heat-sensitive materials, as well as, heat-sensitive biomolecules. Thus, heat-sensitive substrates, such as poly(ethylene terephthalate) (PET) balloon catheters cannot be used with this material. Moreover, molecules such as nucleic acids, proteins, peptides, hormones, heparin and the like are heat-sensitive biomolecules which cannot be exposed to such high temperatures without losing their activity.

The art is not limited, however, to medical devices having lubricous coatings disposed on a surface thereof. Rather, medical articles or devices coated with bio-compatible or bio-active agents have also been described, some of which are set forth below. All of these patents employ various inefficient and/or harsh methods for attaching the bio-compatible/bio-active agent to the surface of a medical article.

For example, U. S. Pat. No. 5,541,167 describes a thrombo-resistant and defoaming coating for blood contacting surfaces including bubble oxygenators, blood filters, etc. This coating includes a commercial preparation of polydimethylsiloxane and silicon dioxide and a quaternary ammonium complex of heparin, such as stearyldimethylbenzyl. This coating, however, suffers from the drawback that the defoaming and heparin components are dissolved in an organic solvent, such as methylene chloride. Such solvents can denature and reduce the bio-activity of bio-active agent, such as heparin. Furthermore, such organic solvent systems produce environmentally hazardous waste, as well as attacking certain polymer substrates.

In a different approach to rendering an implantable medical device bio-compatible, U.S. Pat. No. 5,360,397 describes a porous bio-compatible and bio-stable polyurethane mesh for a catheter made from polycarbonate urethane. This mesh is sputter coated and/or impregnated with a bio-active agent, such as for example, a bactericide. A catheter treated in such a manner, however, is imparted with transient bio-activity at best because the bio-active agent is not covalently bound to the surface thereof. Furthermore, the process of making such a catheter is inefficient because the porous polyurethane mesh must be attached to the surface of the catheter prior to the application of the bio-active agent.

Still further, U.S. Pat. No. 5,263,992 describes a medical device having a bio-compatible coating which includes a bio-compatible agent, such as for example, heparin or streptokinase and a chemical linking moiety. This chemical linking moiety has a structure represented b: A-X-B, wherein A is a photochemically reactive group, B is a reactive group which responds to a different stimulus than A and X is a non-interfering skeletal moiety, such as a $C_1$–$C_{10}$ alkyl. The bio-compatible agent is covalently linked to the surface of the medical device via the linking moiety. In particular, the photochemically reactive group (A) when activated covalently binds to the surface of the medical device. The remaining unreacted reactive group (B) when activated covalently binds to the bio-compatible agent and anchors it to the surface of the medical device. Such devices, however, are difficult and inefficient to produce because they require the use of two separate stimuli to activate the A and B groups of the chemical linking moiety, respectively. Furthermore, the UV light used to activate the A group of the chemical linking moiety for covalently binding it to the surface of a medical device can denature bio-active agents. Such denaturization reduces the bio-activity of such agents and can result in undesirable medical outcomes, such as, clot formation in the case of an anti-thrombogenic agent.

The present invention, however, is directed to hybrid coatings for substrates, particularly medical devices, that function as a bio-compatible surface, as well as a drug delivery vehicle. These coatings are particularly advantageous because they can be applied to devices which are sensitive to high processing temperatures, such as (PET) balloon catheters and other polymeric or heat sensitive materials or biomolecules. Moreover, these coatings also function as therapeutic agent delivery vehicles for delivering such agents to targeted areas in the body. In this regard, the present invention discloses the use of two-component bio-compatible coatings which are both aqueous based. Such coatings are mutually soluble and do not pose the increased medical risks associated with coatings containing organic solvents. Furthermore, preparation of the present aqueous coatings is more efficient because vacuum baking substrates is not required as there are no organic solvents that must be removed. Moreover, because the bio-active surface is covalently bonded to the polymer of the first coating, this coating is permanently attached to the substrate unlike certain of the transient coatings discussed above. Thus, the bio-active surface provides long term bio-compatibility, e.g. thrombo-resistance, while the first coating layer allows a therapeutic agent, i.e. an anti-smooth muscle cell (SMC) proliferation agent to be released which both function to reduce or prevent restenosis of, e.g., an endoprosthesis by minimizing thrombus formation and SMC proliferation.

In summary, the prior art compositions and methods suffer from the drawback that they use organic solvents in their coating layer and/or cure at high temperatures, are transient and/or are inefficient to produce. Thus, there is a need for improved bio-compatible coatings which enhance the bio-compatibility and abrasion-resistance of the surface of heat sensitive medical devices and which also function as therapeutic agent delivery vehicles. The present invention is directed to meeting these and other needs.

SUMMARY OF THE INVENTION

In one embodiment of the present invention there is provided a coating composition for rendering substrates bio-compatible and delivering therapeutic agents in vivo. This coating includes an aqueous dispersion or emulsion of an organic acid functional group-containing polymer and an excess of a polyfunctional crosslinker which is reactive with the organic acid functional groups of the polymer. A therapeutic agent is dispersed within the aqueous dispersion or emulsion. The therapeutic agent is substantially non-reactive with the polymer or the crosslinker. The coating composition also includes an aqueous solution or dispersion of an organic acid functional group-containing bio-active agent or a chemically modified equivalent thereof. The organic acid functional group-containing polymer is covalently bonded to the organic acid functional groups on the bio-active agent through the unreacted excess polyfunctional crosslinker.

Another embodiment is a medical device having a coating on at least a portion of a surface thereof. This coating includes a first layer formed from (a) an aqueous dispersion or emulsion of an organic acid functional group-containing polymer, (b) an excess of a polyfunctional crosslinker which is reactive with the organic acid groups and (c) a therapeutic agent dispersed within the aqueous dispersion or emulsion, wherein the therapeutic agent is substantially non-reactive with (a) or (b). This embodiment also includes a second coating of an aqueous solution or dispersion of an organic acid functional group-containing bio-active agent or a chemically modified equivalent thereof. The first coating is covalently bonded to the second coating through the excess crosslinker and the organic acid functional groups on the second coating so that the therapeutic agent is releasable from the first coating while the second coating, i.e., the bio-active agent substantially remains on a surface of the medical device.

Another embodiment is a method of enhancing the bio-compatibility of a substrate and delivering a therapeutic agent in vivo by providing a continuous bio-compatible surface coating to a surface of the substrate. This method includes applying to the substrate surface a first coating that includes an aqueous dispersion or emulsion of (a) a polymer containing an organic acid functional group, (b) an excess of a polyfunctional crosslinker which is reactive with the organic acid groups of the polymer and (c) a therapeutic agent dispersed within the aqueous dispersion or emulsion, wherein the therapeutic agent is substantially non-reactive with (a) and (b). The first coating is then permitted to dry in order to bind the first coating to the substrate surface, wherein unreacted polyfunctional crosslinker remains present in the crosslinked first coating. A continuous bio-active surface coating is then formed on the substrate by contacting the dried first coating layer with a second coating of an aqueous solution or dispersion of a bio-active agent or a chemically modified equivalent containing an organic acid functional group or a metal salt thereof. The first and second coatings are then dried to covalently bond the organic acid functional groups of the bio-active agent to the polymer through the excess unreacted polyfunctional crosslinker, wherein the therapeutic agent is releasable from the first coating and the bio-active agent substantially remains on the surface to provide enhanced biocompatibility.

Another embodiment includes a multi-layer coating composition for rendering substrates bio-compatible and delivering therapeutic agents in vivo. This embodiment includes a first layer that includes an aqueous polymer dispersion or emulsion, a crosslinker and a therapeutic agent physically dispersed within the dispersion or emulsion, wherein the therapeutic agent is releasable from the first layer and is substantially non-reactive with the polymer or the crosslinker. This coating composition also has a second layer that includes an aqueous solution or dispersion containing a bio-active agent, wherein the polymer of the first layer is covalently bonded to the bio-active agent through the crosslinker.

DETAILED DESCRIPTION OF THE INVENTION

For purposes of the present invention, the term "organic acid functional group" includes any functional group which contains an organic acidic ionizable hydrogen. Examples of such functional groups include free carboxylic, free sulfonic, and free phosphoric acid groups, their metal salts and combinations thereof. Such metal salts include, for example, alkali metal salts like lithium, sodium and potassium salts; alkaline earth metal salts like calcium or magnesium salts; and quaternary amine salts of such acid groups, particularly quaternary ammonium salts.

In the present invention, the organic acid functional group-containing polymer of the aqueous dispersion or emulsion, i.e., first coating composition, is selected based on the nature of the substrate to be coated. The polymer in the first coating composition may be a homo- or copolymer such as, for example, vinyl monomer units, polyurethanes, epoxy resins and combinations thereof.

These classes are merely exemplary and other polymeric materials may be found to be useful.

Preferably, the polymer in the first coating composition may include organic acid functional group-containing polyurethanes, polyacrylates, polymethacrylates, polyisocrotonates, epoxy resins, (meth)acrylate-urethane copolymers and combinations thereof. More preferably, the polymer in the first coating composition includes homo- and copolymers having a substantial amount of organic acid functional groups in their structure. Not wishing to be bound by a particular theory, it is believed that the presence of organic acid functional groups in the polymer act as internal emulsifying agents. A specific class of polyurethanes which are useful in the first coating are the so-called water-borne polyurethanes. Particularly preferred examples of such polyurethanes are internally emulsified water-borne polyurethanes containing internal emulsifiers such as, for example, carboxylic acid, sulfonic acid and/or phosphoric acid groups, including salts of such groups.

Water-borne polyurethanes which are internally emulsified include, for example, those supplied under the trade name NeoRez by Zeneca Resins, including NeoRez-940, NeoRez-972, NeoRez-976 and NeoRez-98 1; those under the trade name Sancure, including Sancure 2026, Sancure 2710, Sancure 1601 and Sancure 899 by B.F. Goodrich; and those under the trade names Bayhydrol LS-2033, Bayhydrol LS-2100, Bayhydrol LS-2990 by Bayer AG. Another example of a type of polymer useful in the first coating composition is the (meth)acrylate-urethane copolymers, including (meth)acrylic urethane copolymer dispersions supplied under the trade names NeoPac E-106, NeoPac E-121, NeoPac E-130 and NeoRez R-973 by Zeneca Resins.

The concentration of the polymer in the first coating is from about 1% to about 60% by weight, and preferably from about 1 % to about 40% by weight. These percent weight values are calculated based on the amount of solid polymer compared to the total weight of the first coating.

The first coating also includes one or more polyfunctional crosslinking agents that are reactive with organic acid functional groups. In the present invention, preferred polyfunctional crosslinking agents include polyfunctional aziridines and polyfunctional carbodiimides.

In the present invention, other crosslinking agents may also be used which include, for example, commercially available preparations sold by Zeneca Resins under the trade name NeoCryl CX 100 and those preparations sold by EIT Industries under the trade name XAMA-7. A commercially available polyfunctional carboimide which is also useful in the present invention is Ucarlink XL-29SE, sold by Union Carbide.

Among the polyfunctional aziridines useful in the present invention are the trifunctional aziridines of the following formula:

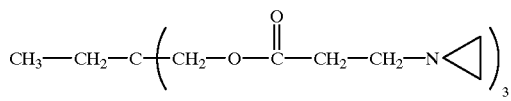

Preferably, the crosslinking agent has more than two functional groups per molecule. Furthermore, the present invention also encompasses a combination of different polyfunctional crosslinking agents.

Not wishing to be bound by a particular theory, it is believed that the functional groups on the crosslinking agent serve at least two purposes. In particular, these groups serve to crosslink the first polymeric coating. Additionally, these groups participate in covalently bonding the second coating to the first coating through reaction with the excess organic acid functional groups on the bio-active agent. Thus, there must be sufficient functionality in the crosslinking agent, e.g. an excess of crosslinking agent, to accomplish both purposes. In particular, there must be a molar excess of crosslinking agent relative to the first coating to ensure that the first coating is substantially crosslinked, and that there are enough unreacted functional groups left on the crosslinking agent to covalently bond the bio-active agent to the first coating.

One indication that insufficient functional groups from the crosslinking agent are present is the inadequate bonding of the second layer to the substrate. This is evidenced by the lack of wear resistance of substrates treated with such a deficient first coating. Furthermore, such coatings are easily wiped off the substrate to which they are applied.

The concentration of the crosslinking agent in the first coating composition is in the range from about 0.2% to about 40% by weight solids content of the first coating, and preferably in the range from about 0.5% to about 20% by weight solids content of the first coating.

The first aqueous coating may include other conventional additives, such as for example, leveling agents, various stabilizers, pH adjustment agents, fillers, defoaming agents and the like, as long as such agents are compatible with the intended use of the coated substrate.

One or more therapeutic agents which are substantially non-reactive with the polymer or crosslinking agent are dispersed within the first aqueous coating. The therapeutic agent is releasable once the substrate is placed within the body. Any therapeutic agent that meets the above-referenced criteria can be dispersed within the first coating. In this regard, the therapeutic agent can be selected from anti-tumor agents, antiviral agents, anti-angiogenic agents, angiogenic agents, anti-mitotic agents, angiostatin agents, endostatin agents, cell cycle regulatory agents, genetic agents, growth hormones, chemically modified equivalents and mixtures thereof.

Desirably, the therapeutic agent is Paclitaxel or a functional equivalent thereof. As used herein, "functional equivalent" includes compositions which act in a similar manner in the body but which may vary structurally. Such functional equivalents include homologs, analogs, derivatives, fragments and pro forms of the therapeutic agent.

In one embodiment, Paclitaxel or a functional equivalent thereof is dispersed within the first coating. Once inside the body, the Paclitaxel is controllably released from the first coating layer into the surrounding environment and functions as a SMC inhibitor which prevents or reduces neointimal growth onto the substrate surface. The result of the controlled release of Paclitaxel or a functional equivalent thereof is to prevent or reduce restenosis of a substrate, i.e. endoprosthesis.

The first coating including the therapeutic agent is applied to a substrate by conventional methods, including dipping and spraying. The first coating is then permitted to dry to obtain a continuous, substantially water-insoluble coating on the surface of the substrate. This coating includes functional groups on the crosslinking agent which are reactive with organic acid groups of the first coating. This dried first coating is contacted with a second aqueous coating which includes an aqueous solution or dispersion of an organic acid functional group-containing bio-active agent. The second coating may be applied over the first coating using the same or different techniques as the first coating. The second coating is then permitted to dry, thereby covalently bonding the organic acid functional group-containing bio-active agent to the first coating via the excess, unreacted functional groups of the crosslinking agent in the first coating. Optionally, the bio-active agent may be incorporated into the first coating in a non-covalent manner. The choice of whether to covalently bond the bio-active agent to the first coating is made with reference to the intended use of the device, the choice of bio-active agent and the composition of the first coating.

Bio-active agents useful in the present invention may be selected from a wide variety of materials provided that they contain at least one organic acid functional group in their structure which can react with the polyfunctional crosslinking agent and still retain bio-active function.

Furthermore, in the case where a particular bio-active agent does not contain at least one organic acid functional group in its structure, a derivative thereof containing such an organic acid functional group is also encompassed by the present invention. The use and synthesis of such derivatives are within the knowledge of those skilled in the art.

Non-limiting classes of useful bio-active agents of the present invention include antithrombogenic agents, antibiotic agents, anti-tumor agents, antiviral agents, anti-angiogenic agents, angiogenic agents, anti-mitotic agents, anti-inflammatory agents, angiostatin agents, endostatin agents, cell cycle regulation agents, genetic agents, including hormones, such as estrogen, their homologues, analogs, derivatives, fragments, pharmaceutical salts and mixtures thereof. Other useful bio-active agents include for example, viral reactors and growth hormones such as Fibroblast Growth Factor and Transforming Growth Factor-β, their homologues, analogs, derivatives, fragments, pharmaceutical salts and mixtures thereof. One specific type of bio-active material useful in the present invention is the class of organic acid functional group-containing polysaccharides.

For purposes of the present invention, such polysaccharides include linear and branched polymers of monosaccharides. The preferred polysaccharide bio-active agents of the present invention are glycosarninoglycans (hereinafter "GAGs").

Glycosaminoglycans are unbranched polysaccharide chains of repeating disaccharide units. One of the repeating disaccharide units is usually an amino sugar (N-acetylglucosamine or N-acetylgalactosarnine) which can be sulfated. The second sugar of the disaccharide unit is usually a uronic acid, such as for example, glucuronic or iduronic acid. Because there are sulfate or carboxyl groups on most of their sugar residues, GAGs are highly negatively charged and are ideal for covalently bonding to the first coating layers via the excess, unreacted functional groups on the crosslinking agent. GAGs which are useful as bio-active agents in the present invention include, for example, heparin, hirudin, heparin sulfate, hyaluronic acid, chondroitin sulfate, dermatan sulfate, keratan sulfate, EPA, prostoctein, reopro, integrin, lytic agents including urokinase and streptokinase, their homologs, analogs, fragments, derivatives and pharmaceutical salts thereof. Other GAG containing molecules are also contemplated by the present invention, for example GAG-containing proteins, such as proteglycans. Desirably, the bio-active agent is heparin or a functional equivalent thereof.

Moreover, the bio-active agent of the present invention can also include organic acid functional group-containing antibiotics. For purposes of the present invention, such antibiotics include penicillins, cephalosporins, vancomycins, aminoglycosides, quinolones, polymyxins, erythromycins, tetracyclines, chloramphenicols, clindamycins, lincomycins, sulfonamides their homologs, analogs, fragments, derivatives, pharmaceutical salts and mixtures thereof.

Additionally, the bio-active agent of the present invention can also include organic acid functional group-containing anti-tumor agents. For purposes of the present invention, such anti-tumor agents include paclitaxel, docetaxel, alkylating agents including mechlorethamine, chlorambucil, cyclophosphamide, melphalan and ifosfarnide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including estrogen, tamoxifen and flutamide their homologs, analogs, fragments, derivatives, pharmaceutical salts and mixtures thereof.

Still further, the bio-active agent of the present invention can include organic acid functional group-containing anti-viral agents. For purposes of the present invention, such anti-viral agents include amantadines, rimantadines, ribavirins, idoxuridines, vidarabines, trifluridines, acyclovirs, ganciclovirs, zidovudines, foscarnets, interferons their homologs, analogs, fragments, derivatives, pharmaceutical salts and mixtures thereof.

In certain cases, such bio-active agents may also become lubricous upon contact with an aqueous medium. Such lubricity will depend on a number of factors, including the type of bio-active agent, its molecular weight, the exposure level to the aqueous medium, as well as the presence of agents which facilitate wetting. In the present invention, the molecular weight of the bio-active agent can vary from fewer than 500 for paclitaxel to about 3,000 to about 30,000 for heparin to an excess of 8,000,000 for hyaluronic acid.

The concentration of the bio-active agent in the second coating composition will typically be from about 0.1% by weight, preferably from about 50% by weight, calculated as solids of bio-active agent compared to the total weight of the second coating composition.

Thus, in one embodiment paclitaxel or a functional equivalent thereof is dispersed within the first coating and is releasable therefrom while heparin is covalently bonded to the polymer of the first coating and remains on the surface of the substrate. In this configuration, the heparin provides the substrate surface of e.g. an endoprosthesis, with excellent thromboresistance while the releasable Paclitaxel coating minimizes SMC proliferation into the endoprosthesis. Functioning together, the heparin and Paclitaxel provide the endoprosthesis with superior resistance to restenosis compared to known bio-compatible coatings.

In another embodiment, the functional groups of the crosslinking agent react with the organic acid functional groups of the polymer in the first coating and the organic acid functional groups of the bio-active agent at a temperature below 120° C. Preferably, these reactions take place between about 10° C. to about 70° C. The drying step for the second coating is chosen based on the substrate and the compositions used in the first and second coatings. Many bio-active agents are temperature sensitive and extreme care must be taken in selecting the appropriate drying temperatures with such agents. For example, when heparin is the bio-active agent, the drying temperature should be no greater than about body temperature.

The selection of the appropriate drying temperature is within the skill of the art given the properties of the substrate and the compositions in the first and second coatings. Preferably, the drying step takes place well below 120° C. If desired, however, and compatible with the nature of the substrate to be coated, higher temperatures may be used, such as for example, when the substrate is metal. Nevertheless, the present invention is designed to be used in coating temperature-sensitive substrates. Thus, the first and second coatings are preferably dried at low temperatures, particularly at ambient or room temperatures, such as for example, at or between about 15° C. and about 35° C. In many cases, drying at about room temperature for about 12 hours will be adequate.

Obviously, the drying time will depend on the drying temperature used, higher drying temperatures requiring shorter drying times and lower drying temperatures requiring longer drying times. As set forth above, it is within the knowledge of a person skilled in the art to determine a suitable combination of drying temperatures and drying times for a specific coating and substrate.

Furthermore, the organic acid functional groups of the crosslinking agent do not necessarily have to have the same reactivity towards the organic acid functional groups of the polymer and bio-active agent in the first and second coatings, respectively. Moreover, the selection of drying conditions will be made with these reactivities in mind.

The bio-active coatings of the present invention may be used to coat a wide range of different substrates. In particular, the bio-active coatings are especially suited for coating at least a portion of a surface of a medical article for use in or on the body, particularly catheters, guidewires, introducer sheaths, trocars and the like, or parts of such articles. More particularly, these coatings may be used to coat endoprostheses including for example, grafts, stents and graft-stent devices. Furthermore, these coatings can be used to coat many different substrates, such as for example, polymeric substrates, non-polymeric substrates, such as metals, and combinations thereof.

For purposes of the present invention, polymeric substrates which rnay be used include, for example, olefin polymers, particularly polyethylene, polypropylene, polyvinylchloride, polytetrafluoroethylene (PTFE), polyvinylacetate, and polystyrene; polyesters, particularly poly(ethylene terephthalate); polyurethanes; polyureas; silicone rubbers; polyamides, particularly nylons; polycarbonates; polyaldehydes; natural rubbers; polyether-ester copolymers such as Hytrel™ and Anitel™; polyether-amide copolymers such as Pebax™; and styrene-butadiene copolymers. Preferably, the polymeric substrate is made from poly(ethylene terephthalate), polyurethane, polyethylene, nylon 6, nylon 11, a polyether-ester copolymer or a polyether-amide copolymer. Shape-memory polymers are also contemplated. The substrate can, of course, be made from other polymers depending upon the intended use thereof and the composition of the first and second coatings. Such a choice of substrate materials is within the knowledge of one skilled in the art.

As set forth above, non-polymeric substrates may also be used in the present invention. These non-polymeric substrates include, for example ceramics, metals, glasses and the like. Furthermore, the substrates of the present invention may include a combination of one or more polymers and/or one or more non-polymers. Examples of metals employed in medical devices include, without limitation, stainless steel, superelastic materials (shape-memory) such as nitinol, gold, silver, titanium, tantulum, platinum and alloys thereof.

In another embodiment of the present invention, a medical device having a coating on at least a portion of a surface thereof is provided for use in conjunction with a body. The bio-active coating includes a first layer as previously described formed from an aqueous dispersion or emulsion of an organic functional group-containing polymer, an excess of a polyfunctional cross-liking agent and therapeutic agent dispersed within the first layer. As set forth previously, the crosslinking agent is reactive with the organic acid groups of the polymer.

The bio-active composition also includes a second coating of an aqueous solution or dispersion which contains an organic acid functional group-containing bio-active agent, as described hereinabove. The first coating is covalently bonded to the second coating through the excess crosslinking agent and the organic acid functional groups on the bio-active coating.

Another embodiment is a method of enhancing the bio-compatibility of a substrate and delivering a therapeutic agent in vivo by providing a continuous bio-compatible surface coating to a surface of the substrate. This method includes applying to the surface a first coating made from (a) a polymer containing an organic acid functional group, (b) an excess of a polyfunctional crosslinker which is reactive with the organic acid groups of the polymer and (c) a therapeutic agent dispersed within the dispersion or emulsion, wherein the therapeutic agent is substantially non-reactive with (a) or (b).

As used herein, "substantially non-reactive" is intended to mean that the therapeutic agent does not or is prevented from covalently bonding to the polymer or crosslinker in a manner which would inhibit its release and biological effectiveness.

The method further includes permitting the first coating to dry as set forth above in order to bind the first coating to the surface of the substrate wherein unreacted polyfunctional crosslinker remains present in the crosslinked first coating. A bio-active surface coating is then formed on the substrate by contacting the dried first coating layer with a second coating of an aqueous solution or dispersion of a bio-active agent or a chemically modified equivalent thereof containing an organic acid functional group or a metal salt thereof. The first and second coatings are then dried to covalently bond the organic acid functional groups of the bio-active agent to the polymer through the excess unreacted polyfunctional crosslinker. Thus, the therapeutic agent is releasable from the first coating and the bio-active agent substantially remains on the surface to provide enhanced bio-compatibility.

In accordance with the present invention, the bio-active agent remains on the surface of the substrate in a biologically active state for a prolonged period of time, such as for example, for the life of the coated substrate.

Another embodiment is a multi-layer coating composition for rendering substrates bio-compatible and delivering therapeutic agents in vivo. This composition includes a first layer of an aqueous polymer dispersion or emulsion, a crosslinker and a therapeutic agent physically dispersed within the dispersion or emulsion. The therapeutic agent(s) is releasable from the first layer and is substantially non-reactive with the polymer or crosslinker.

The multi-layer coating also includes a second layer of an aqueous solution or dispersion containing a bio-active agent, wherein the polymer of the first layer is covalently bonded to the bio-active agent through the crosslinker.

This multi-layer coating composition is applied to the surface of a medical device as described previously. In this embodiment, the bio-active agent remains permanently attached to a surface of the medical device and the therapeutic agent is controllably releasable from the first layer.

In this embodiment, the release of the therapeutic agent may be controlled based on the desired in vivo outcome. Control of release of the therapeutic agent is achieved using various methods including encapsulating the therapeutic agent in biodegradable capsules, varying the amount of crosslinker in the second layer, etc.

The invention will now be further illustrated in the following non-limiting examples representing presently preferred embodiments of the invention.

EXAMPLE 1

A first coating composition is prepared by adding the following ingredients successively to a glass beaker under proper agitation until thoroughly mixed.

| | |
|---|---|
| NeoRez R981 | 250 ml |
| 0.5% Fluorad FC-129 stock solution (prepared by diluting 1 ml Fluora FC-129 in 100 ml of water) | 10 ml |
| 34% NH$_4$OH | 4 ml |
| NeoCryl CX 100 | 20 ml |
| 20% Paclitaxel stock solution (prepared by adding 20 g of Paclitaxel in 100 ml of N-methyl-pyrolidone) | 20 ml |

NeoRez R981 (from Zeneca Resins) is a polyester-based, aliphatic water-borne polyurethane containing carboxylic acid groups, which is stabilized by triethylamine (TEA) and has a solid content of 32% and a ph of 7.5–9.0 at 25° C. It contains a 5.3% N-methyl-pyrrolidone (NMP) as cosolvent. Neocryl CX 100 (from Zeneca Resins) is added as a crosslinker agent. Ammonium hydroxide is used to adjust the pH of the solution. Paclitaxel (from Houser Chemical) is an anti-smooth muscle cell proliferative agent. It is dissolved in NMP as a stock solution.

A second coating composition, as follows, is prepared:

1.2% aqueous solution of sodium heparin (Abbott): 300ml

The above solution is prepared by adding an appropriate amount of heparin powder to 300ml of water under agitation for several hours to obtain a clear homogeneous solution.

A substrate of stainless steel was first cleaned by isopropanol. The stent was spray coated uniformly with first coating composition, and then air dried 30 minutes. Repeat the process until the necessary layer thickness of coating is achieved. The second coating composition was spray coated onto the dried first coating surface and allowed to air dried over night. The coated stent is then put into a 50° C. vacuum oven for 3 hours. The resulted coating has controlled releasable Paclitaxel and covalently bond heparin on surface.

EXAMPLE 2

In the same manner as in Example 1, a first coating composition is prepared using the following ingredients:

| | |
|---|---|
| Bayhydrol PR240 | 250 ml |
| Neocryl CX 100 | 10 ml |
| Triclosan (prepared by dissolving 20 g of Triclosan in 100 ml of NMP) | 50 ml |

Bayhydrol PR240 (from Bayer) is a aliphatic polyurethane dispersion containing sulfonate groups. The waterborne polyurethane supplied has a ph of 6.5–7.5, and the sulfonate groups are in sodium form. The Triclosan (from CIBA-Gaigy), an anti-bacteria agent, is a crystalk powder. 20 g of Triclosan is dissolved in 100 ml of N-methylpyrrolidone.

A second coating composition is prepared in the same manner as in the Example 1:

1.2% sodium heparin (Abbott) aqueous solution.

A substrate of intra-venous dilation catheter is cleaned thoroughly with isoprpanol. The catheter is dipped into the first coating composition, and air dried for 30 minutes. The catheter is then dipped into the second coating composition, and air dried in ambient temperature over night. Subsequently, the catheter is put into a 45° C. vacuum oven for 3 hours. The resulted coating has releasable triclosan and covalently bond heparin on the coating.

EXAMPLE 3

The first coating composition is the same as that in Example 1. The second coating composition iis as follows:

| | |
|---|---|
| 2% hyaluronic acid (sodium salt) aqueous solution | 300 ml |

The 6 grams of hyaluronic acid (sodium salt) (from Sigma) is dissolved in 300ml of water under agitation. Mix thoroughly.

The same coating procedures as in the example 1 are used to apply the first and second coating compositions onto the same stainless steel stent substrate. The resulted coating has controlled releasable Paclitaxel and covalently bond hyaluronic acid on the surface.

The invention being thus described, it will be obvious that the same may be varied in many ways. Such variations are not to be regarded as a departure from the spirit and scope of the invention and, all such modifications are intended to be included within the scope of the following claims.

What is claimed is:

1. A coating composition for rendering substrates biocompatible and delivering therapeutic agents in vivo comprising:
   i. an aqueous dispersion or emulsion of an organic acid functional group-containing polymer and an excess of a polyfunctional crosslinker which is reactive with said organic acid functional groups of said polymer;
   ii. a therapeutic agent dispersed within said aqueous dispersion or emulsion, said therapeutic agent being substantially non-reactive with said polymer or said crosslinker; and
   iii. an aqueous solution or dispersion of an organic acid functional group-containing bio-active agent or equivalent thereof, said polymer covalently bonded to said organic acid functional groups on said bio-active agent through said unreacted excess polyfunctional crosslinker.

2. The coating composition of claim 1, wherein said organic acid functional groups are selected from the group consisting of free carboxylic acid, free sulfonic acid, free phosphoric acid, and combinations thereof.

3. The coating composition of claim 1, wherein said polyfunctional crosslinking agent has more than two functional groups per molecule.

4. The coating composition of claim 1, wherein said polymer is one of an organic acid functional group-containing homo- and copolymer.

5. The coating composition of claim 1, wherein said polymer is selected from the group consisting of polyurethanes, polyacrylates, poly(meth)acrylates, polyisocrotonates, epoxy resins, (meth)acrylate-urethane copolymers and combinations thereof.

6. The coating composition of claim 1, wherein said polymer is a (meth)acrylate-urethane copolymer.

7. The coating composition of claim 1, wherein said polymer is a polyurethane.

8. The coating composition of claim 1, wherein said bio-active agent is selected from the group consisting of anti-thrombogenic agents, antibiotic agents, anti-inflammatory agents, equivalents and mixtures thereof.

9. The coating composition of claim 1, wherein said therapeutic agent is selected from the group consisting of anti-tumor agents, antiviral agents, anti-angiogenic agents, angiogenic agents, anti-mitotic agents, angiostatin agents, endostatin agents, cell cycle regulatory agents, genetic agents, growth hormones, equivalents and mixtures thereof.

10. The coating composition of claim 1, wherein said bio-active agent is an organic acid functional group-containing polysaccharide.

11. The coating composition of claim 10, wherein said polysaccharide is a glycosaminoglycan.

12. The coating composition of claim 11, wherein said glycosaminoglycan is selected from the group consisting of heparin, hirudin, heparin sulfate, hyaluronic acid, chondroitin sulfate, dermatan sulfate, keratin sulfate, prostoctein, reopro, integrin and equivalents thereof.

13. The coating composition of claim 1 wherein said bio-active agent is heparin or a chemically modified equivalent thereof and said therapeutic agent is paclitaxel or equivalent thereof.

14. The coating composition of claim 1, wherein the concentration of said polymer is from about 1% to about 60% by weight solids content.

15. The coating composition of claim 1, wherein the concentration of said polymer is from about 1% to about 40% by weight solids content.

16. The coating composition of claim 1, wherein the concentration of said polyfunctional crosslinker in i. is from about 0.2% to about 40% by weight solids content of said first coating.

17. The coating composition of claim 1, wherein said polymer is covalently bonded to said bio-active agent via said polyfunctional crosslinker at a temperature below about 120° C.

18. The coating composition of claim 1, wherein said polymer is covalently bonded to said bio-active agent via said polyfunctional crosslinker at a temperature between about 10° C. and about 70° C.

19. An implantable device coated with a composition according to claim 1.

20. A medical device having a coating on at least a portion of a surface thereof, said coating comprising:
 i. a first layer formed from (a) an aqueous dispersion or emulsion of an organic acid functional group-containing polymer, (b) an excess of a polyfunctional crosslinker which is reactive with said organic acid groups and (c) a therapeutic agent dispersed within said aqueous dispersion or emulsion, wherein said therapeutic agent is substantially non-reactive with (a) or (b); and
 ii. a second coating of an aqueous solution or dispersion containing an organic acid functional group-containing bio-active agent or equivalent thereof, said first coating covalently bonded to said second coating through said excess crosslinker and said organic acid functional groups on said bio-active coating, wherein said therapeutic agent is releasable from said first coating and said bio-active agent substantially remains on a surface of said medical device.

21. The medical device of claim 20, wherein said surface is selected from the group consisting of polymeric compositions, non-polymeric compositions and combinations thereof.

22. The medical device of claim 20, wherein said surface is selected from the group of consisting of olefin polymers, polyethylene, polypropylene, polyvinyl chloride, polytetrafluoroethylene, polyvinyl acetate, polystyrene, poly(ethylene terephthalate), polyurethane, polyurea, silicone rubbers, polyamides, polycarbonates, polyaldehydes, natural rubbers, polyether-ester copolymers, styrene-butadiene copolymers and combinations thereof.

23. The medical device of claim 20, wherein said surface is selected from the group consisting of ceramics, metals, glasses and combinations thereof.

24. The medical device of claim 20, wherein said device is an endoprosthesis.

25. The medical device of claim 24, wherein said endoprosthesis is selected from the group consisting of grafts, stents and graft-stent devices.

26. The medical device of claim 24, wherein said endoprosthesis is selected from the group consisting of catheters, guidewires, trocars and introducer sheaths.

27. The medical device of claim 20, wherein said bio-active agent is selected from the group consisting of anti-thrombogenic agents, antibiotic agents, anti-inflammatory agents, equivalents and mixtures thereof.

28. The medical device of claim 20, wherein said therapeutic agent is selected from the group consisting of anti-tumor agents, antiviral agents, anti-angiogenic agents, angiogenic agents, anti-mitotic agents, angiostatin agents, endostatin agents, cell cycle regulatory agents, genetic agents, growth hormones, equivalents and mixtures thereof.

29. The medical device of claim 20, wherein said bio-active agent is heparin or a chemically modified equivalent thereof and said therapeutic agent is paclitaxel or equivalent thereof.

30. A multi-layer coating composition for rendering substrates bio-compatible and delivering therapeutic agents in vivo comprising a reaction product of:
 i. a first layer comprising an aqueous polymer dispersion or emulsion, a crosslinker and a therapeutic agent physically dispersed within said dispersion or emulsion, wherein said therapeutic agent is releasable from said first layer and is substantially non-reactive with said polymer or said crosslinker; and
 ii. a second layer comprising an aqueous solution or dispersion containing a bio-active agent, wherein said polymer of said first layer is covalently bonded to said bio-active agent through said crosslinker.

31. The coating composition of claim 30, wherein said polymer and bio-active agent contain organic acid functional groups.

32. The coating composition of claim 30, wherein said crosslinker is a polyfunctional crosslinker which is reactive with said organic acid functional groups of said polymer but not said therapeutic agent.

33. The coating composition of claim 30, wherein said therapeutic agent is paclitaxel or equivalent thereof and said bio-active agent is heparin or equivalent thereof.

34. An implantable medical device having at least a portion of said device coated with said coating according to claim 30, wherein said bio-active agent remains permanently attached to a surface of said medical device while said therapeutic agent is controllably releasable from said first layer.

* * * * *

UNITED STATES PATENT AND TRADEMARK OFFICE
CERTIFICATE OF CORRECTION

PATENT NO.   : 6,179,817 B1
DATED        : January 30, 2001
INVENTOR(S)  : Zhong et al.

It is certified that error appears in the above-identified patent and that said Letters Patent is hereby corrected as shown below:

Column 2,
Lines 27-28, the printed patent in the table incorrectly reads "includes aprotective"; the patent should read -- includes a protective --.

Column 4,
Line 9, the printed patent incorrectly reads "represented b: A-X-B,"; the patent should read -- presented by: A-X-B --.

Column 13,
Line 31, the printed patent in the table incorrectly reads "has a ph of"; the patent should read -- has a pH of --.
Line 33, the printed patent incorrectly reads "is a crystalk powder"; the patent should read -- is a crystal powder --.
Line 40, the printed patent in the table incorrectly reads "with isoprpanol"; the patent should read -- with isopropanol --.
Line 50, the printed patent incorrectly reads "composition iis as"; the patent should read -- composition is as --.

Column 14,
Line 59, the printed patent in the table incorrectly reads "chemically modified equivalent"; the patent should read -- equivalent --.

Signed and Sealed this

First Day of January, 2002

Attest:

Attesting Officer

JAMES E. ROGAN
Director of the United States Patent and Trademark Office